US008821456B2

(12) United States Patent
Daneshvar

(10) Patent No.: US 8,821,456 B2
(45) Date of Patent: Sep. 2, 2014

(54) DANESHVAR MEDICATION PADS, SUPPOSITORIES AND METHODS

(76) Inventor: Yousef Daneshvar, West Bloomfield, MI (US)

(*) Notice: Subject to any disclaimer, the term of this patent is extended or adjusted under 35 U.S.C. 154(b) by 1555 days.

(21) Appl. No.: 11/731,945

(22) Filed: Apr. 2, 2007

(65) Prior Publication Data

US 2007/0287968 A1 Dec. 13, 2007

Related U.S. Application Data

(60) Provisional application No. 60/787,817, filed on Apr. 3, 2006.

(51) Int. Cl.
*A61K 9/02* (2006.01)

(52) U.S. Cl.
USPC ........... 604/288; 604/279; 604/285; 604/358; 604/385.17; 206/529

(58) Field of Classification Search
USPC ......... 604/11, 47, 48, 57, 285–288, 304, 514, 604/515, 517, 275, 278, 279, 358, 385.17; 206/529
See application file for complete search history.

(56) References Cited

U.S. PATENT DOCUMENTS

| 823,499 | A | * | 6/1906 | Barlow | 604/286 |
|---|---|---|---|---|---|
| 1,366,941 | A | * | 2/1921 | Rhodehamel | 424/436 |
| 2,017,334 | A | * | 10/1935 | Ackerman | 604/285 |
| 3,777,755 | A | * | 12/1973 | Groves | 604/286 |
| 3,783,869 | A | * | 1/1974 | Schnipper | 604/304 |
| 4,286,596 | A | * | 9/1981 | Rubinstein | 604/244 |
| 4,445,900 | A | * | 5/1984 | Roeder | 604/389 |
| 4,537,311 | A | * | 8/1985 | Wilkinson et al. | 206/529 |
| 5,263,926 | A | * | 11/1993 | Wilk | 604/11 |
| 6,689,113 | B2 | * | 2/2004 | Boulanger et al. | 604/385.04 |
| 2002/0115976 | A1 | * | 8/2002 | Fleming | 604/385.17 |
| 2003/0050612 | A1 | * | 3/2003 | Mulholland et al. | 604/278 |
| 2003/0120225 | A1 | * | 6/2003 | Everhart et al. | 604/285 |
| 2004/0073184 | A1 | * | 4/2004 | Ohba | 604/385.17 |

* cited by examiner

*Primary Examiner* — Emily Schmidt

(57) ABSTRACT

A medication delivery system for delivering medication to an internal body cavity through a natural body orifice that opens to the cavity has a pad for external placement against the body orifice and an elongated body that extends from the pad through the body orifice when the pad is externally placed against the body orifice. The elongated body carries medication and is long enough to deliver the carried medication to tissue forming the body cavity. The pad has a medication-holding zone surrounding the elongated body on an inner face of the pad and carrying medication that is delivered externally to tissue surrounding the body orifice concurrent with delivery of the medication carried by the elongated body to the tissue forming the body cavity.

5 Claims, 15 Drawing Sheets

DANESHVAR MEDICATION PADS, SUPPOSITORIES AND METHODS

This application incorporates by reference and claims the priority of the provisional application Ser. No. 60/787,817 filed on Apr. 3, 2006.

BACKGROUND OF THIS INVENTION

This invention relates to a new and more effective method of treatment for problems such as hemorrhoids, vulvo-vaginitis, or similar. The reason is the observation by the applicant a physician for many years is that in the regular dressings and medicated gauzes, the medications will be absorbed by the gauze which may diffuse and contaminate the opposing dress or underwear. Also, when used over places such as abscess, and areas that needs drainage, the pressure over the wound may prevent proper draining. In other cases such as hemorrhoids, the problem is both internal and external, which is also true about vaginitis in which case the involvement is the infection and inflammation of both the inner female organ and the external genitalia. In these circumstances using the medication internally may not be effective for the external problems, and may even cause contamination of the adjacent part of the body and underwear. For these reasons a new method of the application of the medicine is introduced which helps the treatments and keeps the adjacent dressing and the underwear clean.

BRIEF EXPLANATION OF THE INVENTION

This is a new means of providing medications for the skin and skin-related problems and some post-surgical cases. This is a wound dressing or pad means which prevents contamination of the dress and underwear and it also provides means similar to massaging the skin in selected cases. These pad means consists of a medicated pad with a layer of non-permeable protective layer outside which this layer will prevent from the medication diffusing from the medicated pad and contaminating the skin of the area. The inner medicated part would help the area to heal so that the skin of the area would be treated in the center and would not contaminate the outside as well. Importantly, the surface of this pad may have raised spots or lines which will work as a means of massaging the skin or parts of the mucosa.

Also, this application introduces new units that are to be used in the anal or vaginal area and that utilize a central piece covered with a layer of absorbent or a media that will hold the medication such as a mesh or a body of sponge. The central piece will be inserted into the anal or vaginal area for allowing its medicated surface to function properly. The central piece has an outer medicated pad as mentioned above which will treat the outside inflamed area. The protective, non-permeable outer cover prevents contamination of the adjacent dress.

THE BRIEF EXPLANATION OF THE DRAWINGS

FIG. 19 Shows a protective cover means for use with the unit shown at FIG. 18 and similar.

DETAILED EXPLANATION OF THE FIGURES

Figure 1:
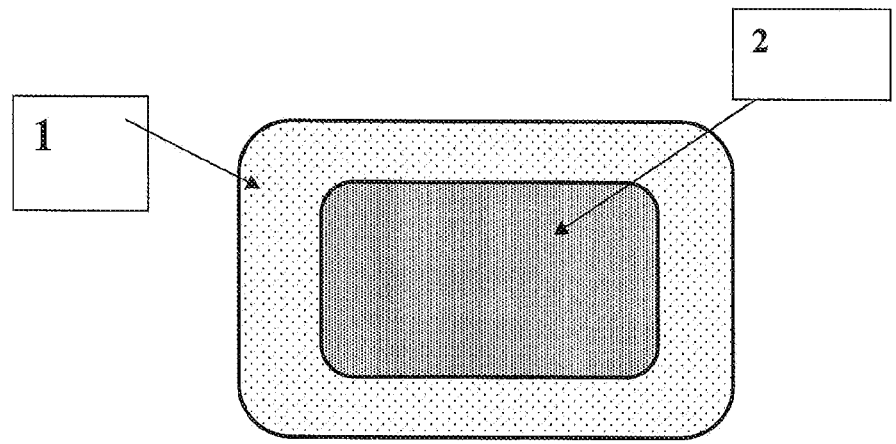
FIG. 1 Shows the top view of a special medicated pad.

FIG. 1 Shows a top view of a special medicated pad, with a central part shown at 2 which is covered with medication. The surrounding area 1 is a soft absorbent layer.

Figure 2:
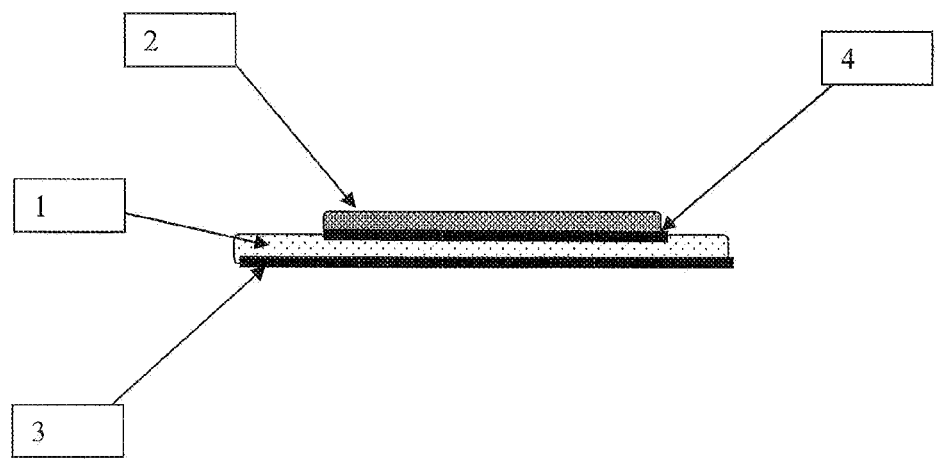
FIG. 2 Shows the cross-cut view of a unit shown in FIG. 1.

FIG. 2 shows the cross-cut view of the unit shown at FIG. 1. In this Figure, the medicated layer is shown at 2 and has a non-permeable layer made from a vinyl or a thin aluminium shown at 4, which does not allow transpassing of the materials. The soft absorbent layer is shown at 1 with a base shown at 3 made of a soft, thin non-permeable layer such as polymer, thin aluminium, or similar material which does not allow transpassing of materials outside.

Figure 3:
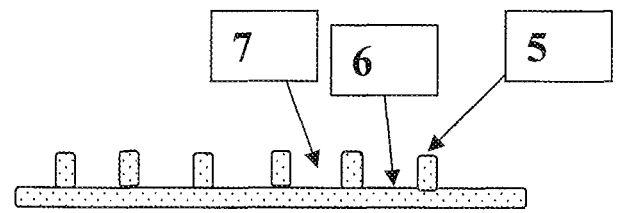
FIGS. 3 and 5 show the cross-cut and the top view of a unit with short walls on its surface.
Figure 5:
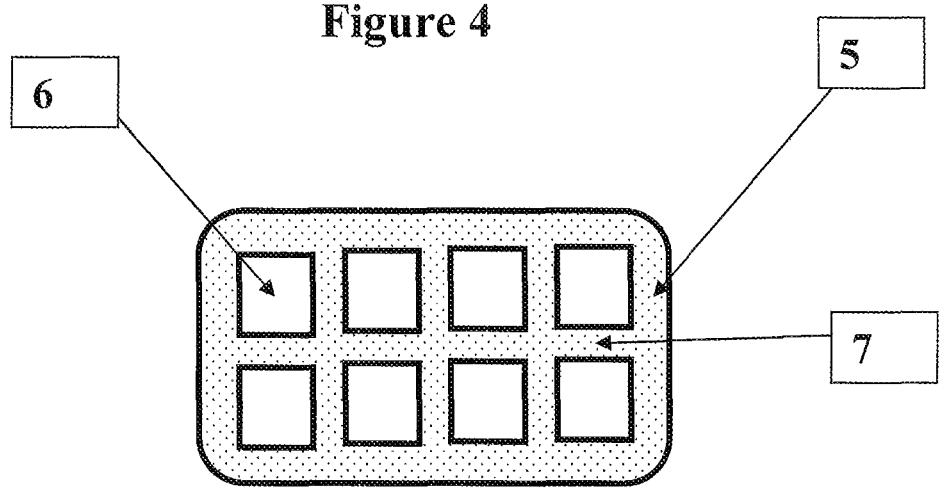

FIGS. 3 and 5 Show the cross-cut view of a unit similar to the one shown in FIGS. 1 and 2, except this model has a series of walls shown at 5, which they create spaces such as space 6 for the medication to be kept. The base of this space is shown at 6. The pattern, size, thickness, height, and relative height of the walls and other characteristics of these walls may vary to make a best possible working model.

Figure 4:
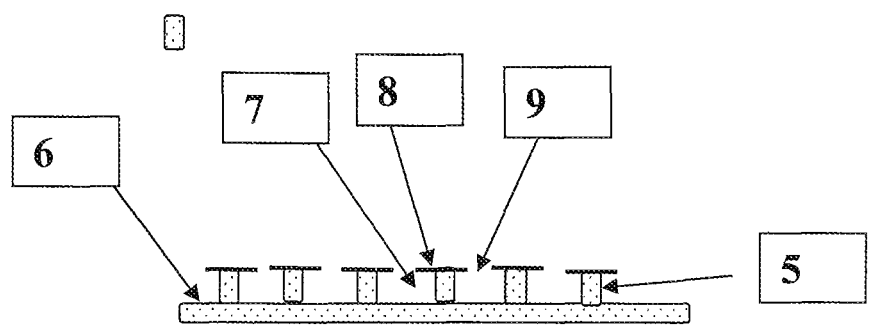
FIG. 4 Shows the cross-cut view of a unit with box shaped spaces and hole on them.

FIG. 4 Shows the cross-cut view of a unit similar to the one shown in FIGS. 3 and 5, except in this model the top of the walls such as 5 has a soft cover 8. The presence of these walls create a box means, 7 with small openings or holes 9 which would allow small amount of the medication to be released from within the box means. This method will make a longer contact between the wound area and the medication and will prevent the medication from being shifted easily from the adjacent area to the side areas due to the pressure or gravity. Importantly, instead of this layer with holes on it, a soft porous layer such as fabric may be used to cover this area to allow slow transpassing of the medication. The base of the medicated area is shown at 6.

Figure 6:
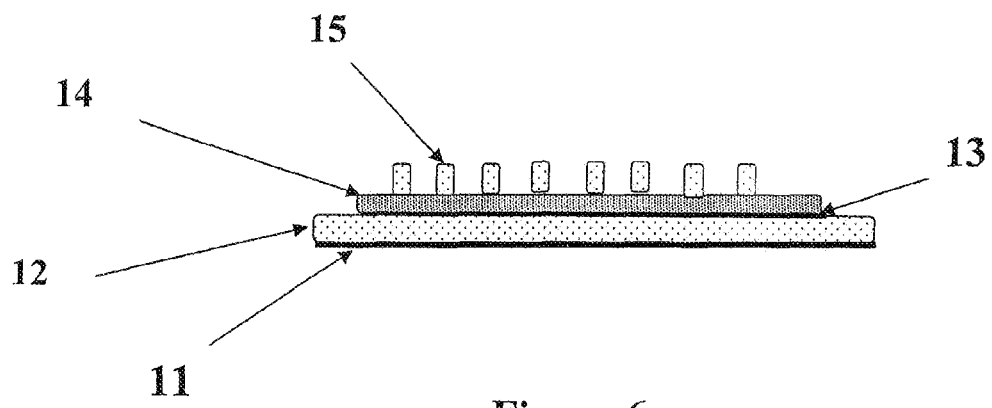
FIG. 6 Shows a unit with a series of small bumps on its surface.

FIG. 6 Shows a cross-cut view of a unit similar to the ones shown in FIGS. 1 and 2, except in this unit the surface of the medicated area has a raised means such as bumps, vegetations or raised spots which will function to gently massage the surface of the wound area for debridement or excitement of the wound as explained in the text. In this Figure the medicated layer is shown at 14 with one vegetation shown at 15. The non-permeable vinyl or thin aluminium layer under the medicated area is shown at 13. The soft absorbent layer is shown at 12. The outer non-permeable layer is shown at 11.

Figure 7:
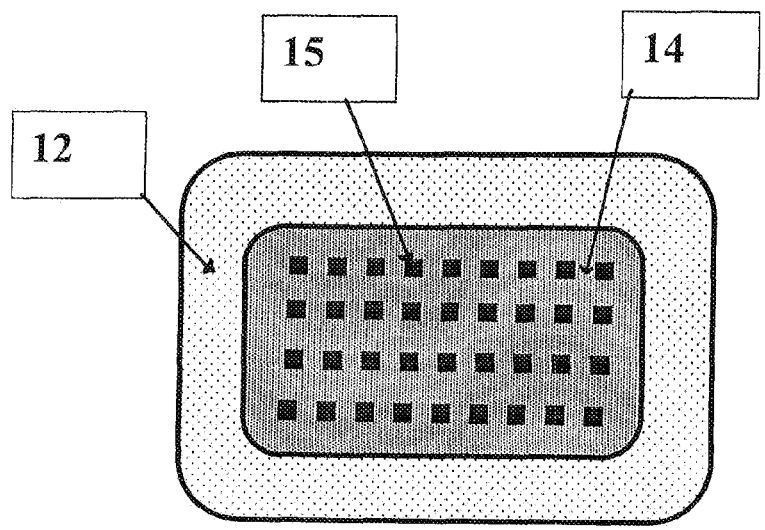
FIG. 7 Shows a top view of a unit shown at FIG. 6.

FIG. 7 Shows the top surface of the unit shown in FIG. 6. In this Figure, the medicated layer is shown at 14 with one vegetation shown at 15. The soft absorbent layer is shown at 12.

Figure 8:
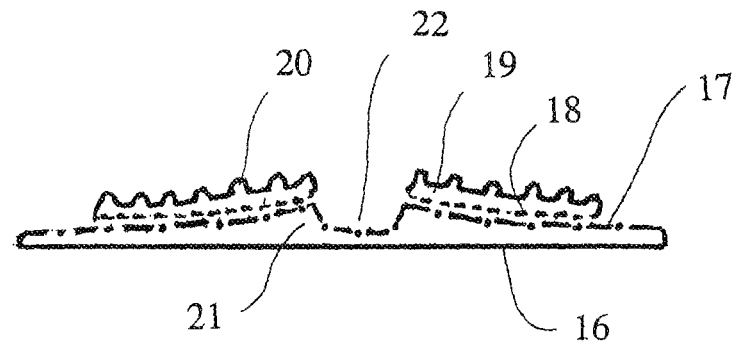
FIG. 8 Shows a unit with an empty space in its center for drainage of the pus.

FIG. 8 shows a cross-cut view of a unit similar to the unit shown at FIG. 6, except this unit has a thicker absorbent layer 17 with its raised center area 21 which has an empty space 22 in it. The empty space of the unit allows the drainage of an abscess or a wound with secretions with ease, since the opening of the center would not compress the opening of the abscess or wound and thus the pus will empty into the space. In this Figure, the medicated layer is shown at 19 with its non-permeable outer layer 18 and one vegetation shown at 20. The soft absorbent layer 17 with its thicker center piece 21 surrounds the empty space 22. The non-permeable outer layer is shown at 16.

Figure 9:
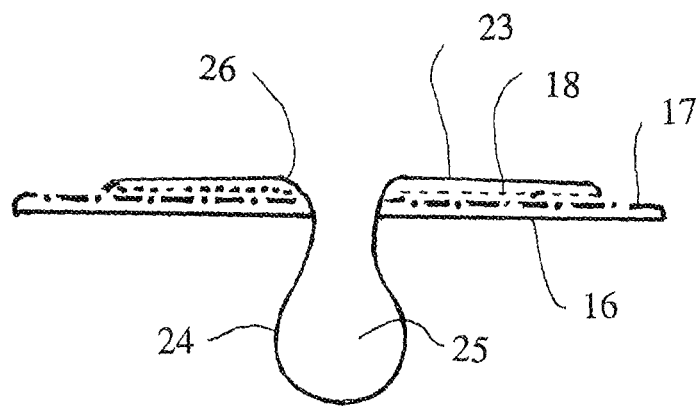
FIG. 9 Shows a unit with a suction bulb in the center for suctioning the pus from the center of an abscess.

FIG. 9 illustrates a unit for suctioning pus or secretions from an abscess or wound. This unit is basically very similar to the one shown in FIG. 8, except in this Figure a suction bulb 24 is constructed in the center to create a vacuum and suction the pus or the drainage out of the wound. In this Figure, the medicated layer is shown at 23 with the base of the suction bulb shown at 26 and its empty space at 25.

Figure 10:
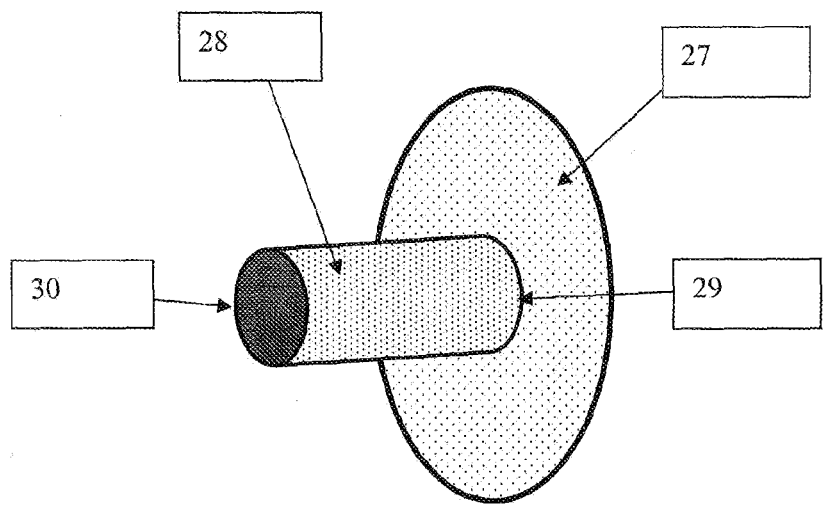
FIG. 10 Shows a unit in which the suppository part is like a condom.

FIG. 10 Shows a unit that has a base part 27 for standing outside of body orifice (such as vulvar areas in women) and am empty part 28 that is similar to a condom covered with a layer of medication. This unit will accept an insert such as one shown at FIG. 11 which is designed to give a shape, hardness and body in order to enter to the orifice of the patient and to function as a proper and more effective suppository means. In this Figure, the external medication pad is shown at 27 and holds a hollow piece 28 made from layer, a fabric, a porous or a non absorbent material which will hold the medication. This piece is shown at 28, its outside end is shown at 30, and an inner opening at 29. The outside surface of the body, 28 of this unit may have walls for holding the medication properly. These walls will make spaces which may be covered at a membrane to help medication to be applied evenly. The surface of this piece 28 may be made to have bumps, raised lines or spots of any form, to allow a gentle massage of the area and mucosa as is explained in the text. The size, thickness, color, the consistency, relative sizes, other characteristics of this unit, and all its components may vary to make it more effective.

Figure 11:
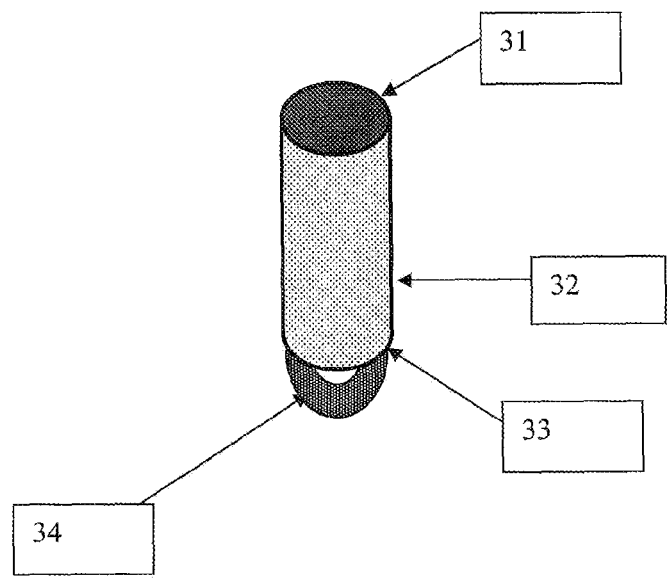
FIG. 11 Shows an insert designed to fit inside the condom of the previous figure.

FIG. 11. Shows an insert means designed for being inserted into the opening and the inner space of piece 28 from FIG. 10. This insert may have a shape such as a suppository, a cone or a cylinderical shape, or a cylinder that is pressed to be somewhat flat or similar. This insert may be made from sponge, foam, plastic means, an inflatable balloon, or anything similar that can give the needed shape and consistency to this unit. This Figure shows that this unit has a tip 31 and body 32, outer end 33, and handle 34. The size, thickness, color, consistency, relative sizes, and other characteristics of this unit, and all its components may vary to make it more effective.

Figure 12:
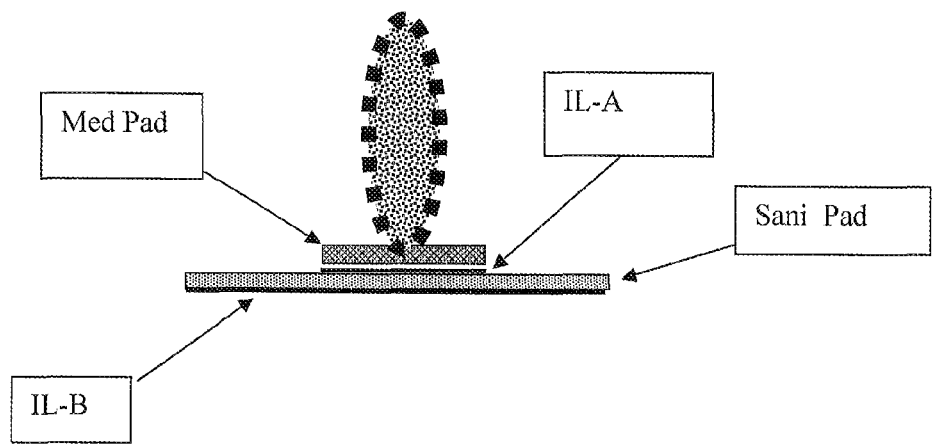
FIG. 12 Shows the cross cut view of a special medicated pad and suppository.
Figure 14:
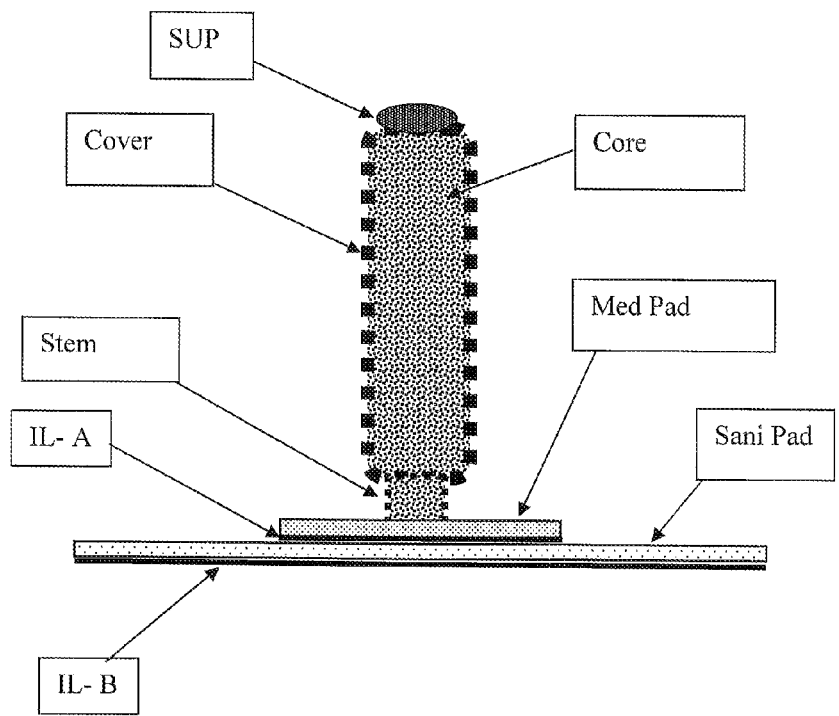
FIG. 14 Shows a cross-cut view of a suppository unit with a rather cylinderical shape and a central core.

FIG. 12. Shows a schematically the vertical cross-cut view of a suppository unit for use in the ano-rectal area. This unit consist of a suppository piece, SUP which has a central core for holding the unit stable for the process of insertion into the rectal area, a more detailed of such unit is shown at FIG. 14. This unit also has an outer surface for holding the medication, Med for delivery into the rectal area. The medication will be held on the surface of this unit by various means. The base of this unit has a medicated pad, Med Pad which is designed to hold medication for the application in the peri-anal area. The Med Pad consist a soft layer on its upper, central surface for holding the medication for the peri-anal area. This part may have a layer of impermeable layer shown at IL-A made from a layer of polymer or thin aluminium or similar, under in order to prevent the medication to leak to sani pad, Sani Pad. The sani pad is another pad means which is a larger layer made from a non-irritant, absorbent layer in order to prevent from contamination of the area surrounding the anal area. This piece has a layer of impermeable layer shown at IL-B made from a polymer, thin aluminium or similar material for preventing from the medication from leaking out from this area, so that it will prevent from the contamination of the underwear.

Importantly, in some models the pad means may only consist of the sani pad, Sani Pad and not to have the medication pad, Med Pad. Also Importantly, in some figures such as the FIGS. 23 and 24 only the sani pad, Sani Pad is shown. However, the applicant would like to indicate that those models also every model indicated in this application may have Sani Pad alone or with the Medi Pad with it.

Figure 13:
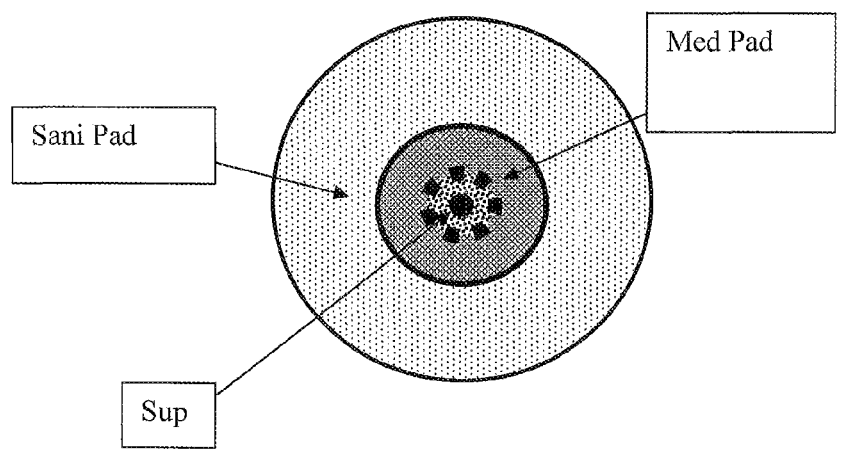
FIG. 13 Shows the top view of a unit shown in FIG. 12.

FIG. 13. Shows the top view of the unit shown in FIG. 12. In this Figure the suppository piece, SUP is in the center, and the medicated pad, Med Pad is seen in the center around the suppository, SUP. The soft, absorbent pad, Sani Pad is shown around the medication pad, Med Pad.

FIG. 14. Shows schematically a cross-cut view of a unit similar to the unit shown at FIG. 12, except in this model the unit has a different shape, it is more cylinderical with a medicated tip to smooth the end of the cylinder and make the process of the insertion to the rectal area smooth. This unit also has a stem, Stem that connects the body of the suppository, Sup to the pads and keeps it stable.

In this model the unit has a core, Core which is in the center of the suppository and has a covered surface, Cover which functions as a holding means for the medication so that it is a delivery means for the medication for to anal area. This cover may have different thickness and may be made from different materials, fabric, waxes, foams etc, and may have different designs.

The medication pad, Med Pad and the Sani Pad have the same basic make up as shown in FIG. 12, and is explained in the text.

Figure 15:
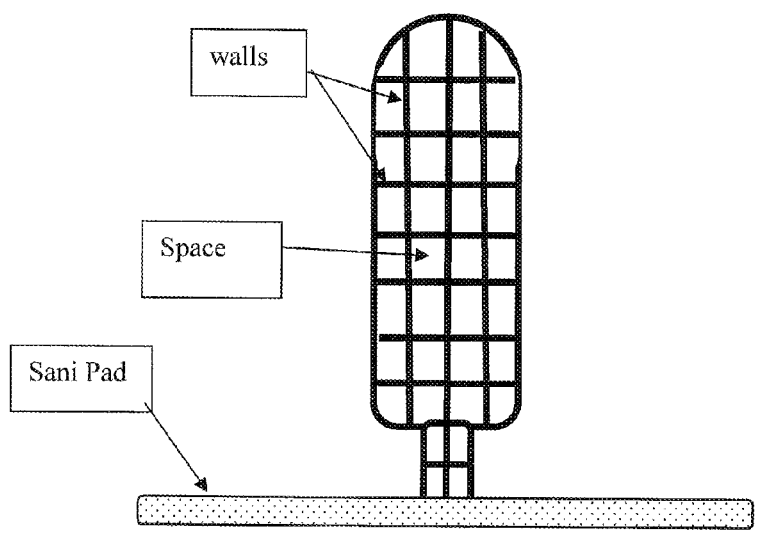
FIG. 15 Shows the side view of a suppository unit that has walls on its surface creating small spaces for holding medication.

FIG. 15. Shows schematically the outer surface of a suppository means similar to the unit shown at previous FIG. 14. which consist of a core means with a different outer cover or surface. The core means is similar to the core means shown at previous FIG. 14 and it is to provide shape, body and consistency to the suppository. The outer surface however, has a series of walls, Wall that are arranged in a vertical and horizontal directions which make a series of small spaces, Space, designed for holding a predicated amount of medication for delivery to the ano-rectal area. This method prevents medications from moving down and away from the adjacent surface due to gravity, or focal pressure, thus it makes the medication more available for the small area that each space faces.

Figure 16:
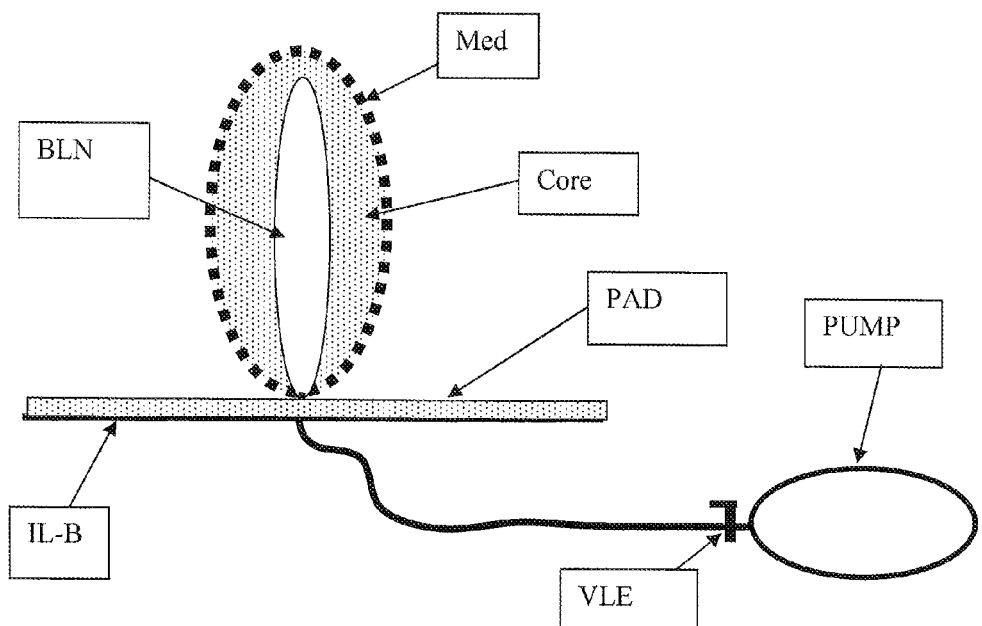
FIG. 16 Shows a cross-cut view of a suppository unit that has an inflatable balloon in it for being expandable.

FIG. 16. Shows schematically a suppository means that has an expandable body powered with another expandable unit such as a balloon, BLN inside, so that the balloon can be inflated to a larger size. The unit may have a medi pad and sani pad which in this figure are collectively shown as the pad means, PAD. The balloon means has a tubing connected to a pump, PUMP, and a valve means, VLE which allows the tubing to the balloon to be closed after the inflation of the balloon. This unit has the advantage that it allows the unit to be inserted in smaller condition then to be inflated to enlarge. This will be useful in cases which the presence of acute process and swelling a larger unit can not be placed in the area without endurance of pain, discomfort and trauma. Thus initially the unit can be inserted in a deflated condition so that after the initial effect of the medication with its comforting and healing effect allows the unit to be inflated to open the folds of the involved tissues, to compress the veins and provide the medication to the whole site of the anorectal area for a more effective effect.

Importantly, the size, shape and other characteristics of this unit may be different to match the needs of patients. Importantly, the balloon may be chosen to have some bulged shape inside the anal area above the sphincter to hold it in place securely and effectively. This will be very important to prevent incontinence. The balloon may be inflated by a syringe and a valve will keep the air inside.

Figure 17:
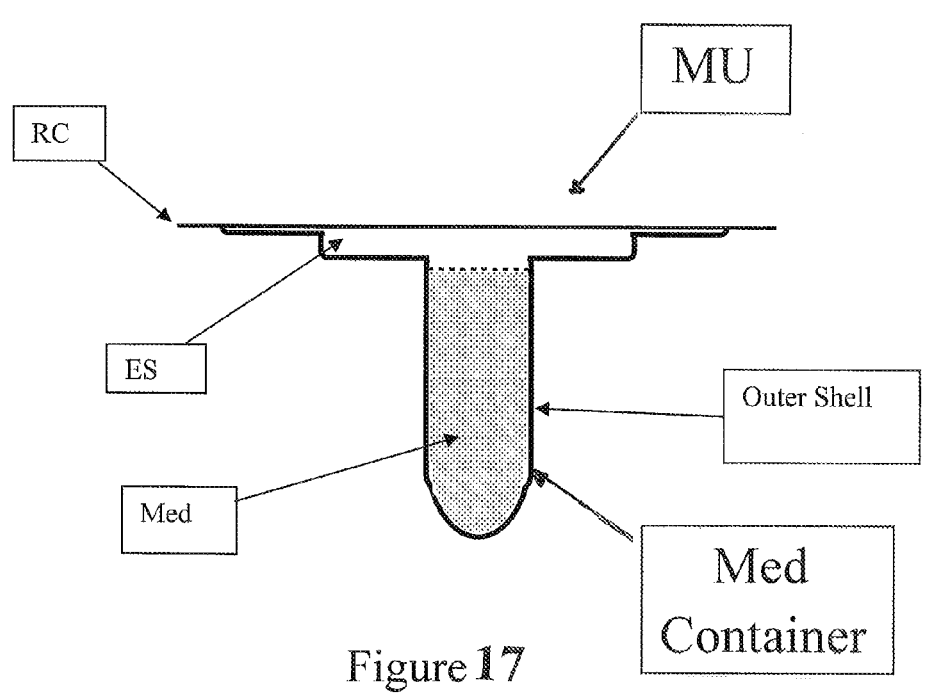
FIG. 17 Shows a medication holding means and a delivery system for use with a dry suppository means and medication pad.

FIG. 17. Shows a method of delivery or the application of the medication to a dry suppository pad means, referred to as the Med Unit. This method provides a financial advantage, because the medication pad and suppository can be kept dry, without having the medication on their surfaces. This provides the advantages that many of these pads can be kept in a volume packed, and sterilized condition for use rather than individually wrapped and ready for use. However, the user will have the option of 1. To apply the medication from a tube to the dry suppository pad means, which can be done except for problems such as the difficulty of application of medication by an individual who has, visual, neuro-muscular or arthritic problems and is not able to have the job done right or on timely basis.

2. To use a Med Unit, MU, shown in this figure. The med unit allows a uniform, structured application of the medication to the surface of a matching dry suppository pad means, shown at FIG. 18, and therefore functions as an applicator for applying medicine to the suppository pad means. In this model the Med Unit is a shaped container, Med Container, whose shape matches the shape and the size of the matching suppository pad means. The inner space of this medication container, Med Container, provides a receptacle that will be almost filled by medication, Med as shown, to function as a cradle filled with medication for the dry suppository, pad means to fit in. At the time of use a dry suppository pad means will be inserted into this unit so that its surface will be covered with the medication.

The reason why the medication is not filled to the top of the medication container is due to the calculation that with the insertion of the dry suppository pad means the medication will move out and overflow to fill the empty space, ES base area in order to reach to the surface of the medi pad, Med Pad, as shown in FIGS. 14 and 15. A removable protective cover, RC will keep the open surface of the Med Unit protected from the germs and micro particles. Thus with this design, the unit allows the application of the medication to the suppository as well as the medication pad, of a unit similar to the unit shown at FIG. 18. This unit will be provided with medication in a sterile condition. It may be more of a series of these attached to each other in its borders.

Method of Use

At the time of use the user will follow the following steps.

1. The user will remove the removeable cover, RC from the Med Unit and expose the medication for use.

2. Holding the medication pad and suppository unit in one hand the user will insert the tip of the dry suppository piece such as one similar to the unit shown at FIG. 18 into the Med Unit with another hand pushing till the tip of the suppository reaches the deepest point of the Med Unit. At the end of this step.

A. The surface of the suppository with be covered with the medication.

B. The suppository will push the surplus of the medication out into the space, ES. This surplus then will contact the adjacent central part of the sani pad, Sani Pad area from the unit shown at FIG. 17 or to the medication pad, Med Pad shown units shown at FIGS. 12-13 So that it will deliver the medication to the external hemorrhoid, either by the central zone of the Sani Pad from FIG. 17 or Med Pad from FIGS. 12-13. for best result as explained in the text.

3. The user will the remove the empty body of the Med Unit which is out of medication and use the medicated suppository pad means.

This method has the following advantages.

1. Allows the use of these units to be economical.

2. Allows the dry medication pad and suppository to be used with different medications.

3. Will make the process of the application of medication simple and easy.

4. Will prevent from wasting of medication.

Figure 18:
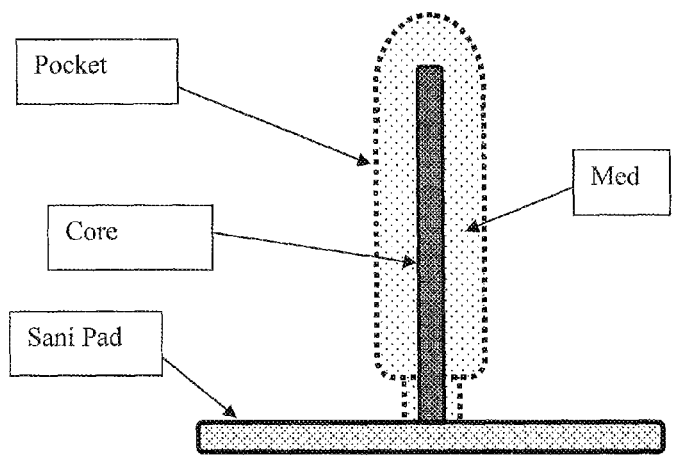
FIG. 18 Shows a suppository means that has medication inside a porous pocket and with a relatively hard core for keeping the unit in shape for the initial use.

FIG. 18. Shows schematically a different model of the suppository delivery system which consist of the following.

1. A suppository means made of a porous cover means that will act as pocket, Pocket and will keep the medication, Med inside it. Initially this medication will be a rather waxy type material that is solid in room temp but when warms up inside the body will loosen to be in a liquid condition and to ooze out of the porous cover gradually and to be disposed to the surrounding ano-rectal area. The consistency of the waxy medication will allow the unit to have a body and hardness to this unit for the initial insertion. Although in some cases the unit may also have a more rigid piece in itself marked as a Core so that the core will help in having a body for this unit in order to be inserted inside the body. The unit also has a pad means, Sani Pad as well. A sani pad, Sani Pad may also be added to this unit. This unit has the following advantages.

A. This method allows a long period of delivery of medication to the area.

B. The body of the unit will shrink to be small and thus would not create a potential problem in the area if a larger unit could cause.

Importantly, the cover of this unit may be made to be absorbed or disintegration with time. And the body of the core, Core to soften with temp as well.

Importantly, any other means that can be utilized with this unit to keep the mediation in shape for delivery and gradual delivery of it to the ano-rectal area may be used with this unit.

Figure 19:
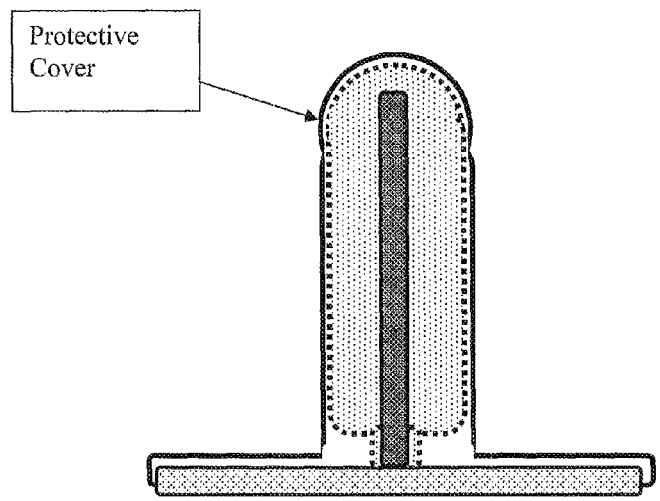

FIG. 19. Shows schematically a protective cover means, Protective Cover which is designed to go over the units shown in this application. In the figure the protective cover, Protective Cover is applied over the unit shown at previous FIG. 17. This unit may be made from a layer of aluminum foil, a thin polymer or similar materials. It will cover the whole medication pad-suppository unit and will prevent it from contamination. This unit may be made to keep the suppository in a bent position compared to the base.

Figure 20:
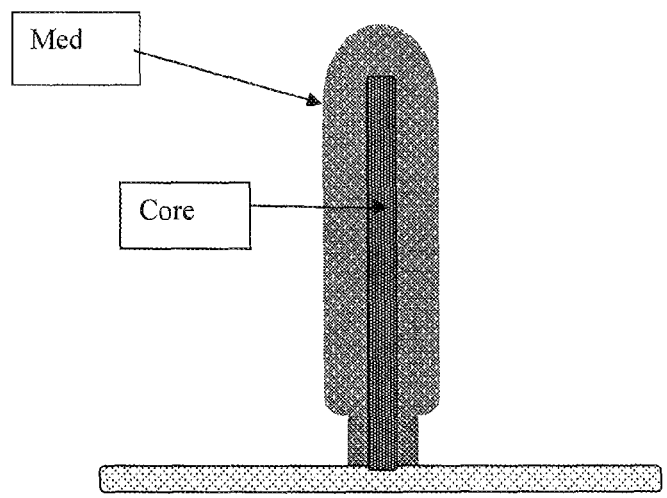
FIG. 20 Shows the cross-cut of a suppository means with waxy medication hold in place by a relatively hard core.
Figure 21:
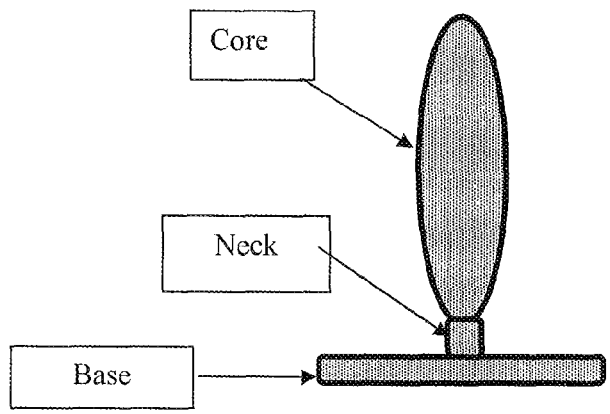
FIG. 21 shows the front view of a core means made of a relatively rigid material for holding medication as a suppository means, for use with a pad means.

FIG. 20. Shows schematically a model of medication delivery system in the shape of suppository, which the medication, Med has a waxy consistency that is solid in outside temp but when warms up inside the body it will loosen to be delivered to the surrounding ano-rectal area. The consistency of the waxy medication will keep the body of this unit hard and proper for the initial delivery. The unit may be further supported by a body of a rather semi rigid, core that is connected to the pad. Importantly, the connection to the pad will prevent the core unit to be loose after the med is dissolved. This unit also has a sani pad means that is attached to this unit for cleanness as explained in the text. FIG. 21. Shows schematically an insert or a core means, Core, designed for placement inside an absorbent or impermeable mesh in order to make a unit for carrying the medication into the anorectal area. This unit is made from a relatively semi rigid material such as a polymer, rubber, latex or any other synthetic material that will fit the purpose for such use. This unit consist of the following pieces.

a. A suppository piece, Core that has a shape and design for insertion and function as a suppository core.

b. A base, Base that is designed for being placed in the outer surface of the sani pad in order to prevent from dislodgement and movement of the Core to the upper part of the rectum. This base is a rather 1-1.5 inches long piece of the polymer that has the thickness of a match and will align in the anal area between the buttocks.

c. A neck, Stem that connects the Core to the base, Base. This part will be a relatively flexible piece that allows the Core to bend compared with the base.

Figure 23:
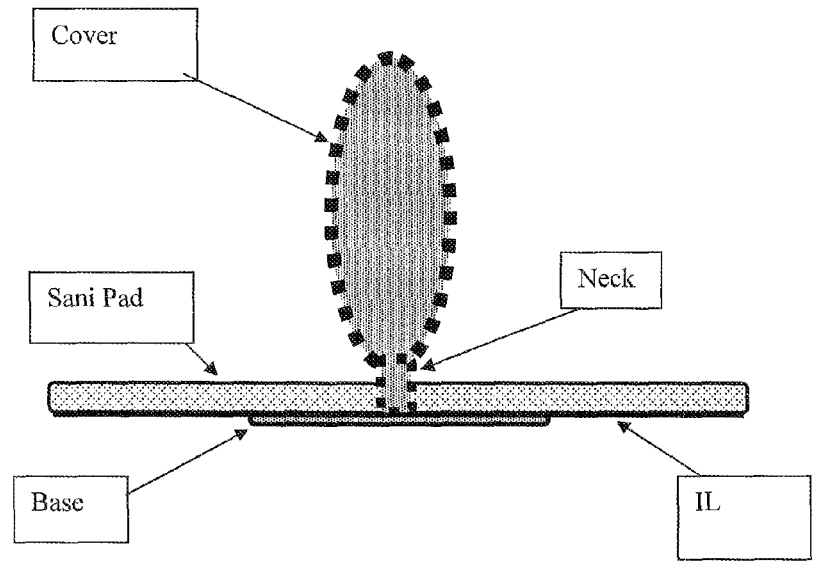
FIG. 23 shows the unit shown at FIG. 21 with cover and a med pad attached to it.

The Core of this piece will be placed via a hole in the center of the Sani Pad, to be functional, as shown in FIG. 23. The base, Base will prevent the Core from breaking and moving away from the Sani Pad.

Figure 22:
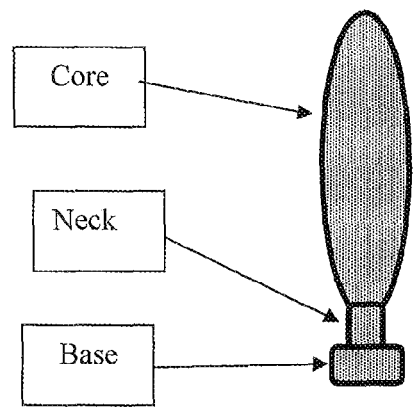
FIG. 22 shows the side view of the unit shown at FIG. 21.

FIG. 22. Shows schematically the side view of the insert shown in previous FIG. 21. In this figure the Core, neck piece, Stem is shown and the Base is also shown and reveals its narrow width. By comparing FIG. 21 and FIG. 22, it can be seen that the Base has different diameters in different diametrical directions that make the shape narrower between one pair of opposite sides and wider between another pair of opposite sides.

FIG. 23. Shows schematically a functional dry model of a medication pad and suppository unit which consist of the following.

1. A suppository piece made from covering a Core of an insert with a layer of absorbent or impermeable mesh, Cover. So that the combination allows this unit to accept, hold and deliver a medication that needs to be delivered to the anorectal area.

2. A clean, pad means, Sani Pad that consist of a layer of soft non-irritant absorbent means which also has a thin layer of impermeable material at its lower/outer surface. This layer will function to prevent the medicine from leaking out and contaminating the dress.

3. The body of the suppository means of this unit is moved from the outer surface of the Sani Pad to its inner surface via a hole that is in the center of the Sani Pad. Importantly, suppository means has a base, Base which is a long narrow piece attached to the neck which is designed to not to pass thorough the hole of the Sani Pad means since the length of this piece will prevent from such a move. Importantly, the long but narrow body of the base, Base allows it to be placed in the anno-rectal area along the space between the buttocks and to be tolerated well.

4. The neck piece is also covered with mesh and stays in the anal area. This makes a dry med pad suppository unit that is ready for the placement of the medication on its surface for use. The unit similar to the unit shown at FIG. 17 will be used in order to apply medication to the outer surface of the suppository part, the neck and the center of the Sani Pad.

Please note that the shape of suppository means can be made different, as shown in different figures.

Figure 24:
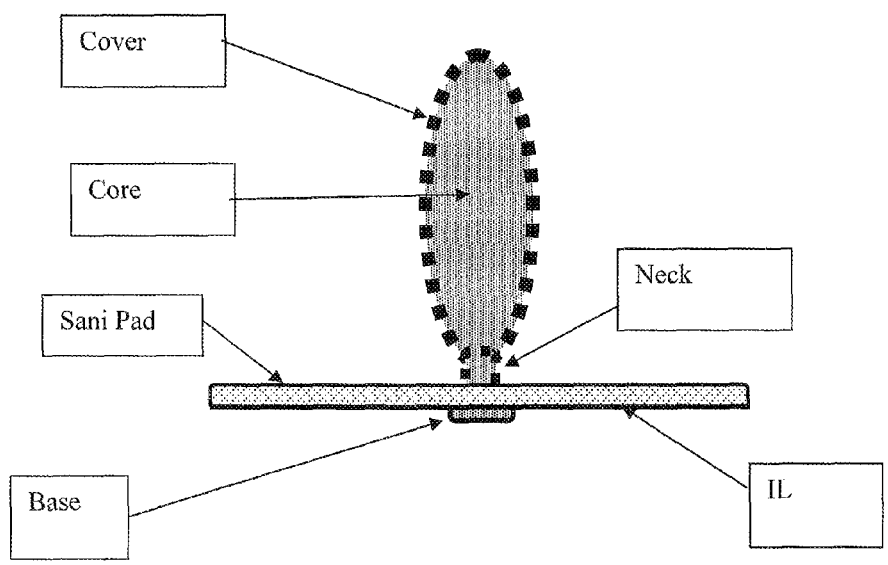
FIG. 24 shows another side view of the unit shown at FIG. 23.

FIG. 24. Shows schematically the side view of the suppository means shown in previous FIG. 23. In this figure the cover means, Cover, the core means, Core, and the neck piece, Neck are shown. The neck piece goes thorough the Sani Pad. The base, Base of the insert means prevents that core to move away from the Sani Pad and entering into the anal area. The Sani Pad is shown with its impermeable layer, IL.

Figure 25:
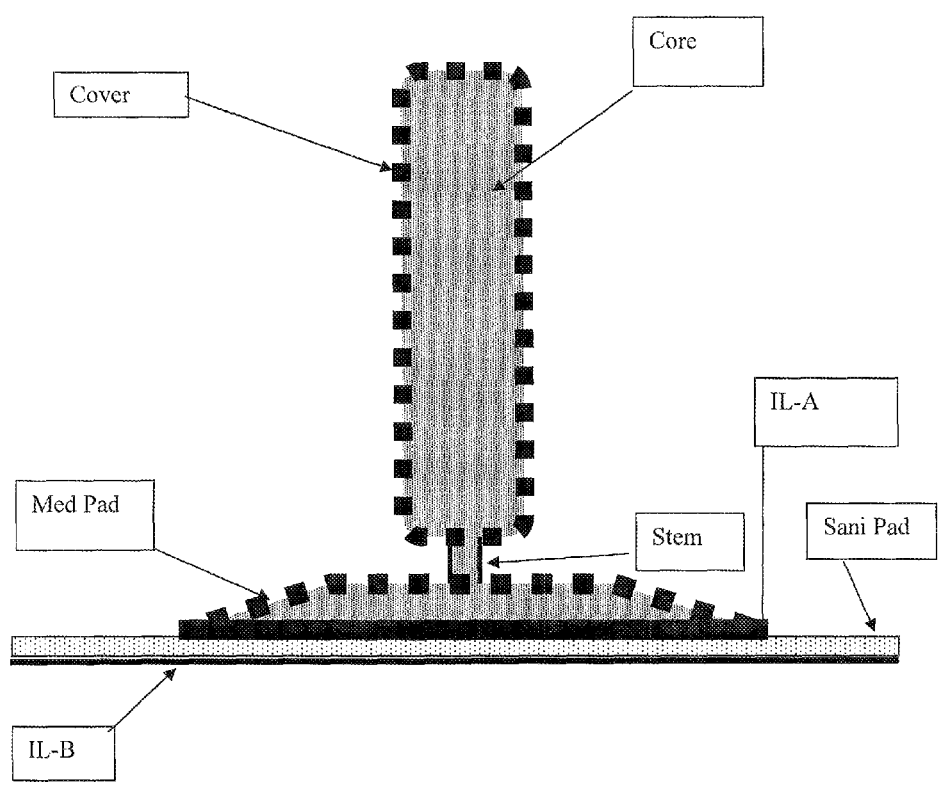
FIG. 25 shows a cross-cut of a medication delivery system for the vulvo-vaginal area.

FIG. 25. Shows schematically a cross-cut view of a unit for use in the vulvo-vaginal area. This unit is similar to the unit shown at FIG. 12 except it is modified for use in the vulva vaginal area of the ladies for the treatment of the inflammation, infection and similar problems. This unit consist of the following.

A. A insert piece for the vagina, which has a core, Core which provides the body for holding the unit stable for the insertion into the vagina and filling the area, in order to expand the area and open the tissue foldings for exposure to the medication. This piece has an outer cover, Cover, designed for holding the medication for delivery the walls of the vagina. The medication will be held on the surface of this unit by various means explained in the text.

B. This unit also has a medicated pad, Med Pad in the base, for holding medication for the application in the vulvar area. The Med Pad is larger and is more prominent than the Med Pad for the anno rectal area. This part consist a rather larger and more prominent soft layer which will fit the size of the outer part of the female area, the labia and the external genitalia of the ladies. This part may have short walls, indentations, raised areas etc. Not only for holding the medication for the vulvar area but also for unfolding and presence in the folded tissues for providing medication. So that the exposure of the tissue to the medication will reduce the itching and irritation. This method provides medication to all affected areas of females in these condition. This part may have a layer of impermeable layer shown at IL-A made from a layer of polymer or thin aluminium or similar to prevent from medication from reaching the absorbent layer.

C. The unit has another pad means, Sani Pad which is even larger than the medicated pad area. This piece is made from a non-irritant, absorbent, soft layer in order to prevent from contamination of the area surrounding the vulvar area.

D. This piece also has a layer of impermeable layer shown at IL-B made from a layer of polymer, thin aluminium or similar material to prevent from the medication from leaking out from the Sani Pad and contaminate the underwear.

E. A short neck, Stem attaches the insert piece to the pad means and prevents the insert to get loose and move up. The neck is flexible and allows the insert to bent.

Figure 26:
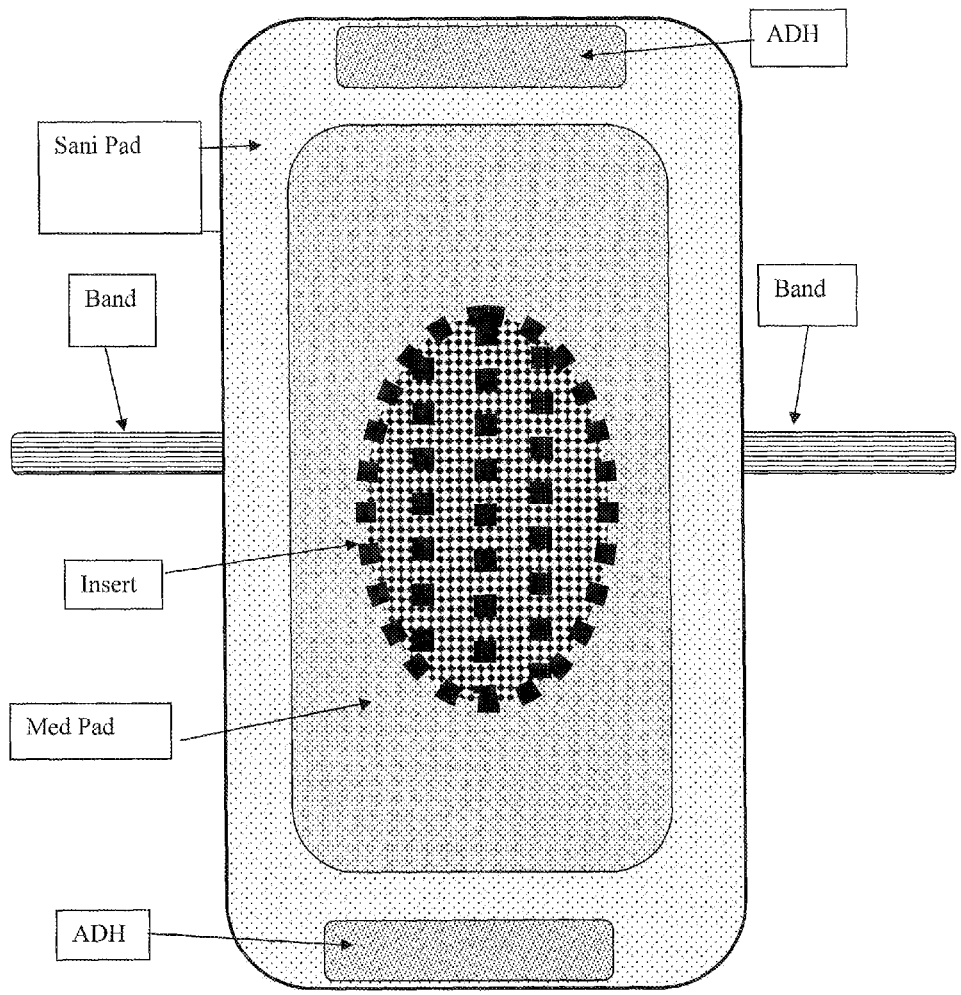
FIG. 26 shows the top side view of a unit similar to one shown at FIG. 25.

FIG. 26 shows the top view of the unit similar to one shown at FIG. 25. In this view the insert, Insert, the medication pad, Med Pad and the sani pad, Sani Pad are shown, which are also similar to the sani pad suppository means shown at previous figures. However, this figure also shows that zones of adhesive shown at ADH that allows this unit to be adhered to the body of the user for preventing it from falling in wrong place.

Also the unit may have bands, Band which allows the unit to be tied to the body for preventing from accidental fall of the used unit in a wrong place. This figure shows the relative size of the insert which will also have the cover means for medication. It shows the extension of the medication pad, Med Pad to the sides so that it will be large enough to cover the external genitalia of the ladies. And the sani pad, Sani Pad that will also extend to cover the sides of the Med Pad so that it will prevent from contamination of the skin. Please note that the size, shape and the characteristics of this unit and its components will vary to allow the most useful unit to be made for the use.

Figure 27:
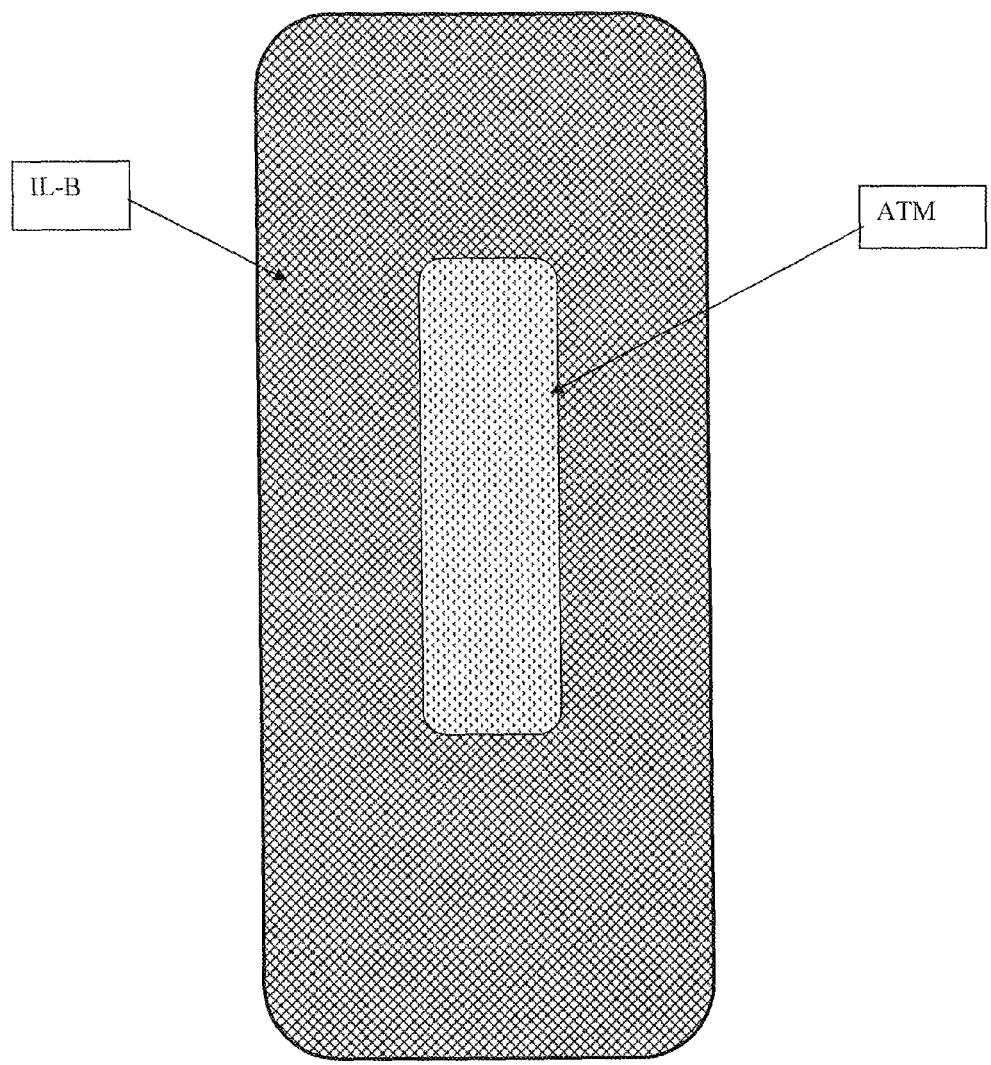
FIG. 27 shows a lower surface of a medication delivery system for the vulvo-vaginal area. Which has attachment means.

FIG. 27 shows a outer or the other surface of a medication delivery system for the vulvo-vaginal area, shown at previous FIG. 25. In this figure the impermeable layer, IL-B is shown with a zone of attachment means, ATM on it. This zone can be made from a hook, fastener attachment means that will attach to a body of the underwear or a matching zone of loop fastener attachment means located inside the underwear of the user. So that this attachment will prevent this unit from falling in a wrong place.

Detailed Explanation of this Invention

Human life is complicated with problems of many forms. One common problem relates to skin and its related orifices. Sometimes these problems are due to infection and inflammations and other times they are part of treatments and surgeries. Commonly, chronic dermatitis and cases such as psoriasis occur which need treatment and dressing of the area. Commonly, these medications are applied with the use of gauzes and gauze pads. However, the applicant believes that this method is not the best since there are problems such as:

First, the gauzes absorb an amount of mediations which are expensive. Second, they commonly allow the medications to leak outside causing contamination of the opposing dresses to occur.

Third, naturally gauzes would cause the medications to move from the pressed area to the less pressurized area to cause lesser amount of medications to be present in the pressed areas.

Fourth, gravity may also play a role as well. In cases which the medication can drip, it will do so, and medication will move from upper parts to lower ones, so that the upper parts of the wound would not receive enough medications and in the lower areas the extra medication will be wasted.

Also importantly, the applicant believes that the secretions and crusts of the wound or inflamed areas can play an important role in preventing proper application of the medication to the needed area. The hard crusts, pusses, secretions and similar stuff would prevent the medications from reaching to the needed tissues. Also importantly, many times the inflamed area itches and feels better if scratched. Having these points in mind, this applicant, a medical doctor introduces the following means of application of medications. These units are designed to provide medication for the skin and skin related problems, in cases of infections, wounds, chronic skin problems, such as psoriasis, surgical cases, and treatment of problems of certain orifices of the body such as the rectum and the vagina. The main unit which is referred as a "Medicated Pad." is shown at FIGS. 1 & 2. This pad consist of 1. A non-permeable layer outside shown at FIGS. 2 at 3 is made from a thin layer of a polymer, a vinyl, aluminum, latex or similar material. This layer prevents medications, secretions, pus etc . . . from oozing outside and contaminating the nearby skin and dressing. This layer will be soft and thin. It may be chosen to have some memory such as the aluminium to accept and hold the shape of the area. Or without memory to allow it fit the shape of the area, such as units made from latex or vinyl.

2. A Layer A absorbent layer 1, shown at FIGS. 1 & 2 on its surface. This layer of absorbent is designed to absorb the secretions and medications that may leak from the sides of the medicated area and will contaminate the skin and related parts. Thus this layer will absorb any materials such as medications, pus, secretions and similar materials that come in contact with it.

3. A layer of non-permeable layer 4 shown at FIG. 2, which will prevent the medication from leaking, oozing, or diffusing from a medicated surface 1. Since otherwise the absorbing layer 1 from FIGS. 1 and 2 will absorb the medication from the medication layer 2. This design will prevent from wasting medication, and allows the medication to be available in the most needed area.

4. A soft layer 2 shown at FIGS. 1 & 2 which contains the medication that is be applied to the skin or wound area. This piece allows the medication to be applied over it and exposed to the needed area. The application of the medicine may be done before (by the pharmaceutical company) or at the time of use by the patient.

Importantly, these units will be modified to serve different purposes as well. For example, in some of these models, as shown in FIGS. 6 and 7, the surface of the medicated part will be chosen to have a series of raised bumps, spots, vegetations, and lines of different shapes and sizes. These will be made from soft polymers, woven materials, etc. so that the combination will create a function such as massaging the involved area, and so that it will play a role in the combinations of the following functions:

1. To massage the area of inflammation which in some or many cases has tendency to itch and irritate, so that this massage will have a soothing effect and will provide relief.

2. To have a massaging effect in the area for helping the secretions and crusts of the inflamed area to be gently removed and the base of the affected area to be exposed to medication. Thus the medication contact with the inflamed area will promote healing.

3. To have the folds of the inflamed area to be turned gently in order for medication to reach the tissue, which otherwise would not have been reached, if, for example, the flat dressing had been utilized.

Importantly, the size, shape, the numbers and consistency of these units as well as other characteristics and specifics of these pieces will vary to allow the best functional units for each job to be made.

Importantly, in some models as shown at FIGS. 3-7 the surface area will have a series of walls made from polymers, woven materials, rubber, waxes or similar for creating small spaces. These spaces are designed for holding the medications, so that this method will allow massaging of the mucosa as well as allowing the medication to be delivered more evenly in the area to prevent the medication from moving due to gravity or local pressure of dressing. The size and relative sizes of these walls, shape, number and consistency of these walls as well as the other specifics and characteristics of constructions of these walls may vary from unit to unit. In some models as shown at FIGS. 3-5 the walls of the unit may have also shorter walls parallel to the base in order to create more secluded spaces for placement of the medications and for even slower release of the medication.

These units with some modifications may also be properly used in some other conditions in medicine such as abscesses or after surgeries and certain wounds in which the site of the wound needs to be drained to have pus and other secretions to be emptied from the wound. As shown in FIGS. 10 and 11. In such cases it would be better to have a unit that has an opening in front of the center of the abscess or along the cut of the wound. For this purpose, a model of these units will be made with an open area in their center to allow the pus to drain out into this open space of this unit. This is to facilitate drainage of the secretions out of the wound into the open space. The applicant believes that if it is desired that pus or other secretions be drained from the area, then the opening of the wound should not be pressed by using a flat dressing since this process may press the fluid from the center into the surrounding tissues (in the skin wall) to some degree. Therefore, the applicant suggests the use of suction bulbs as shown in FIG. 11 or similar means to facilitate draining of the wound. The inner space of these suction bulbs may contain a soft mesh of absorbing material to absorb and hold the pus inside itself. In some cases, this function may be done by connecting the center of the unit to a suction machine, a vacuum bottle, or a similar unit by proper tubing or similar means as well. In such cases, the edges of the wound will be pressed to be sealed by the balloons.

Also, the applicant believes a gentle, but continuous, pressure around, or in the periphery of, the abscess or wound area by a doughnut-shaped balloon or series of properly arranged bubbles may be very useful to help in drainage of the wound. Perhaps it should be mentioned that many times in medicine the pus is squeezed out of its pocket or sac by manually squeezing the area. Now, if we apply a gentle, but continuous, pressure around the abscess and wound and also leave its opening free, or by connecting it to a vacuum, there will be better drainage.

Importantly, the pressure to the area may be applied by connecting the sides of these balloons or bubbles unit to an elastic strap that will go around a limb or an area to pull the balloons or bubbles down toward the skin of the involved area in order to create the needed pressure. In some cases, elastic wraps may be connected to the sides of longer balloons or bubble units to pull them as needed. A non-stretchable strap connected to the sides of the balloons may also perform this job if used properly. Alternatively, and for this purpose, a doughnut-shaped balloon or another similar balloon means will be connected to the rear surface of this model of medication pad, and be strapped or wrapped by non-stretchable or elastic bands so that it will be conveniently held in place to function properly. This will also be very useful for some other conditions, such as after certain surgeries or wounds, to help the drainage to occur. Naturally, if the wound is long, then the shape of this piece has to be long as well with a long matching open center. It also has to have the length and proper thickness for use in these areas. Naturally, special skills and attention with state of the art knowledge and calculations will be used to make the construction of such units to be the best and functional.

Also, importantly, in order to allow better shaping of the dressing to occur in some models the outside cover of the unit may be made from aluminium to accept the shape of the area and to stay in place easily. Also, in other models this outer layer may be made from a layer of latex in order to allow the unit to accept and adjust to the shape of the area easily so that when the unit is used in an awkward place, it can accept the shape of the area to work well. For example, a unit that is to cover the tip of the elbow, when made from latex, will fit the joint better to cover this area well and, importantly, to allow the joint to function easily and properly.

Importantly, this unit may be modified slightly to be useful in cases of a wound with a cut on the skin. In such case, the unit will be made to have a cut in the middle with pieces of elastic or rubber bands going from one side to another to allow these parts to be pulled together as shown in FIGS. 8 & 9. This construction will pull these two pieces to each other in order to bring the edges of the cut skin together and still will allow the cut area to be covered by medication. This is believed to simplify the treatment many times and may avoid the need for suturing in some cases. The reason that this model will work, but the regular dressing may not work as well, is that the small bumps of these covers may be made that collectively function to stick to the skin and pull it gently to bring its edges together and to keep the edges of the cuts close to each other to heal. Naturally, this will be for cases in which the skin is loose enough to come together easily. In other cases, of course, the skin will need to be corrected surgically.

Importantly, this goal can also be achieved by utilizing springs in the construction of this model so that the release of such springs will bring the separate pieces of this unit and the underlying skin together. The tips of these springs may be chosen to be somewhat sharp to enter the skin superficially to help in pulling the skin together.

Importantly, in order to hold these units in place, in some models of the medication pads, such units may be made to have bands, straps, or wraps and held in the needed place securely. Interestingly, sleeves made from latex (which is introduced in one of my applications) may also be very conveniently utilized to be part of the units construction to allow this job to be done. In such cases, the outer surface of the medication pads will be connected to the inner surface of the latex sleeves. In such cases, the latex layer may assume the role of the "A" layer. In some other models, this unit may have a rim covered by adhesive around the outer non-permeable layer that will allow the unit to be held in place. In practice, this part as well as the surface of the whole pad, may be covered by a protective layer of plastic that will be peeled off to expose the unit for use.

This unit can be made to be used in many conditions such as patches of psoriasis, chronic dermatitis, etc. In all of these, there will be a suitable unit to be used. Importantly, the construction of this unit will allow the unit to be cut to fit the size of the area.

Importantly, along with some modification of the shape of this unit, special units will be made to help in a very disturbing condition for the men commonly referred to as "The Jock Itch".

For this condition, a unit will be made to fit the area and have a shape to hold the scrotum in the center and to have medicated flaps to fit in between the scrotum and the mid/upper thigh skin. This unit will have the needed medication protected by a removable plastic layer and will be readily available for the patients to buy and use. This unit will fit inside the men's shorts to be held in place securely or it may have a band to go around the waist as well.

Importantly, in some cases this unit may be made to have only the outer non-permeable unit overed by the soft cover which may be medicated in the center.

Explanation of Some Other Units

The unit which was mentioned above may be also used effectively in cases such as hemorrhoid or vulvo-vaginitis. This is of special interest and importance since the applicant believes that the use of commonly used suppositories in such cases carries a significant problem for example in the case of hemorrhoid: since the problem commonly is not only due to inflammation of the inner hemorrhoid but also an external one as well, thus the use of suppository will not be enough for the whole problem. Also, the effect of the suppository in the area will be less when they can melt and the medication more. The use of suppositories has the trouble of causing contamination of the related underwear which is unpleasant, bothersome, and unwanted. The same is almost true about the inflammation of the vagina in women. First many times in this condition not only is the inner part of the vagina inflamed, but the outside of the vagina and the connected mucosa are involved and inflamed as well. A condition recognized as vulvo-vaginitis. In such cases, commonly the treatment is to use medications in the form of suppositories or placement of medicated creams. However, these medications do not cover the outside mucosa, and thus will be less effective. Even when used inside the vagina, it has the problem of soiling and contaminating the underwear if the medication leaks out, which is unpleasant, unwanted and embarrassing. For such reasons, this inventor introduces a method and means of delivering medication to these areas and similar conditions which is different and believed to be better. These models introduce a means of providing medication for the anal or vaginal area that is delivered in the shape of a suppository connected to an outer medicated pad as well, as shown in figures. In this method, a non-absorbent mesh made from plastic, latex, rubber, fabric or any other synthetic suitable non-absorbable material will be utilized to make a body to hold a medication with the consistency of a wax formed to be in the shape of a suppository, cone, cylindrical shape, etc. Importantly, the medication may also be held inside a small pocket (in the shape of a suppository) of a mesh or membrane inside the outer mesh in order to allow a means or mechanism to deliver the needed medication slowly. This whole unit is to function to deliver the medication and then to be disposed. This body, however, will be specially designed to allow a rather gradual delivery of the medication to occur and to make contact of the inflamed and/or infected area with the medication to be a longer process. At times, the outer surface of this mesh or body may also be chosen to have a rubbing or massaging function as well to allow the mucosa to be scratched gently to feel better and also to open the folds of the mucosa to expose them to the medication. These units will also be made to have a mass or volume in order to stretch the area gently to allow all of the mucosa to be exposed to medication as well. Also, different parts of the mucosa of the involved area will be exposed to the medication. At times, these models with vegetations or raised spots on them can also be very useful in moving the secretions away from the surface of the mucosa and to allow the affected surface to be exposed to medications as explained earlier. These are believed to cause a better treatment and better feeling as well. This suppository piece will be connected to the surface of a special medicated pad that has its own important role in order to help the outside inflamed area to heal and also to prevent the garments from being dirtied.

The main parts of this unit will be explained as follows:

The Outer Medicated Pad

These units solve problems that commonly accompany the hemorrhoids, vulvo-vaginitis and similar surgical problems. In such cases the application of the medication internally not only may not reach every inflamed or infected areas but also the medication may diffuse and contaminate the opposing dress or underwear. Also, importantly hemorrhoids and vulvo-vaginitis the affected areas are both internal and external thus the use of medication internally will not be effective for the external problems most of the times and it will contamination the underwear. For such reasons this new method combines the use of the suppository with means of application of medicine to the adjacent and the external areas for a more effective treatment. This units consist of the following.

1. A pad means reffered as sanitation pad or sani pad as shown in FIGS. 12 and 13 that consist of a soft, absorbent layer that will stand in area surrounding the suppository means. This layer will be a comfortable means which stay around the anal area.

The pad means has a protective cover outside, made from a thin layer of impermeable material, IL-B such as vinyl, aluminium, latex etc., that prevents from leaking of the oily material and secretions outside and the contamination of the skin. The central part of the sani pad may hold some amount of the medication for delivering to the anal area.

2. A smaller pad means, which is a medicated pad, Med Pad shown in FIGS. 12 and 13 which is located in the center of the Sani Pad. This pad will hold medication for application to the anal or vaginal area. The Med Pad consist a soft layer for holding the medication for the anal area, also it may have a layer of impermeable layer shown at IL-A made from a layer of polymer or thin aluminium or similar.

Importantly, the medicated pad may be omitted in some models. Also in some models the medicated pads may not have the impermeable layer, IL-A The Sani Pad and its related parts will provide the following functions:

I. Providing medication to the skin and mucosa around the orifice.

II. Prevent from the leakage of the medication so that there will be no soiling of the underwear or the garment.

III. May provide a gentle massage in the inflamed area in cases which such function would be helpful.

IV. To cause the medication to come in contact with the folds of the outside area.

Importantly, in some cases the outer medication pad of this unit may be made to have only a non-permeable layer covered with the soft non irritant layer, which may be medicated in the center.

Explanation of the Suppository Part

The job of this part is holding the medication inside or on its surface to deliver to the inner body effectively. Basically, this part has a shape of a commonly used suppository or a modified cylinder with soft rounded edges. This may even be in the shape of a cone or any other suitable or properly designed new shapes. This suppository piece may have a central core to give a volume and a body, in order to hold the medication inside and/or over itself. This body can be made from a mesh of polymer, waxy material, fabric or any other kinds of synthetic materials that will function for this purpose. It will function as follows:

1. This piece is to provide a body to the unit in order to have a volume so that at the time of use it will cause some stretching of the wall for providing medication to the folded mucosa. So that the mucosa will be more spread to allow the medication to become more evenly spread on the surface of the involved area.

2. The unit may have a surface with bumps, raised spots, vegetations or walls various nature on its surface in order to provide a rubbing effect in the area, to unfold the mucosa, provide better treatment and improvement. Importantly, the small vegetations will also function to remove/dislodge the secretions from the surface of the mucosa and allow the medication to touch the surface of the mucosa and be more effective.

4. In a model of this unit has a design of an outer pad with a layer of material with an empty space inside, designed for holding the medication on its surface. Which to some degree it will be similar to the shape of a commonly used condom. This model gives the option of changing the center piece/core that fits inside it. Thus, in these models a differently sized and shaped inner piece/core can be inserted into the outer unit to give the needed and desired shape to the body.

The center core of these units may be made from foam, rubber any other polymer or even from a balloon that can be inflated to the size. Naturally, the size of this unit will be different to match the size of the patient who uses it. Importantly, the balloon may be chosen to have some bulged shape inside the anal area above the sphincter to hold it in place securely and effectively. This will be very important to prevent incontinence.

Thus a medicated pads may be made with a hollow center part similar to an appropriately sized, condom with a shape and size to make the insertion of an inner core possible. This core will have a body or a means to give shape and consistency to this unit so that it will be reasonably hard and consistent enough to be inserted in the needed orifice (here the vagina). This inner core may be made from sponge, plastic, balloon, rubber, latex, or any other similar and their combinations.

This will be shaped to match the need and be utilized as needed. This plan would make it inner core be utilized frequently with the medicated part, which by its nature will be disposable. A lubricant material may be used to allow the insertion process of the core to the hollow condom to be done easily. It is to be said that the condom part may be made to be an expandable unit similar to a balloon that, with inflation, will assume the wanted shape. This part may have an inflation port or tube with a needed valve and may be inflated by any possible means, as well as blowing it by mouth or using syringes for this purpose.

5. Importantly, A balloon shaped unit will be very useful for providing medication in the colon when there is a need for treatment of the wall of the colon. Importantly, the unit may be made to allow the medication to be delivered, slowly by oozing gradually from the center of an expandable unit outside to its surface. In such case the wall of the unit will have small openings to allow the diffusion of the medication gradually.

6. Importantly, the surface of this suppository as well as the surface of the medicated part of the base may have walls of various nature to create small spaces for holding the medications inside. These small spaces will create a unit a box that will prevent from the free flow of the medications due to gravity, pressure any other reasons. This will give the chance for the medications to be distributed more evenly.

7. In some models, the suppository part may be made in the form of a mesh, so that it will hold the medication inside and allow the medication to diffuse outside and be delivered slowly and gradually to the desired area.

8. The unit may have a central core as shown at FIGS. 21 and 22.

This body, suppository, or mesh will be connected to the center of a medicated pad as shown in multiple figures, which has its own important construction, function and structure. The surface of the medicated pad will have the needed medications for treatment of the outside of the orifice such as external hemorrhoids or vulvar area when involved. This pad, due to its outside protective cover, will prevent contamination of the outside skin as well so that the skin of the area would be treated in the center with a protected outside area.

A protective cover may be used to surface of these units, that will be removed before use.

Importantly, in cases in which the outside area does not need medication, the pad means will have an outer surface covered with a non-permeable layer and a soft cover over it, to prevent the contamination of the underwear.

In some models, the unit will come without medication so that the medication can be applied by the patient prior to use. Such medications may be packaged with the unit, or they may be purchased separately. Also, in some models the surface of the suppository unit may be chosen to be bare for the patient to apply the mediation on the surface of the plastic or latex surface of this unit.

The function of the suppository is a as follows

1. It will be a delivery means of medications to the anal area and its adjacent area. This may be made of A. Medication to be in the form of waxes so that it will keep its relatively hard shape during the insertion to the rectum, then to start melting after it is in the warmer condition of the rectum. A core means to be used to keep the wax means in connection with the sani pad.

B. The suppository to be made by keeping the medication inside a pocket of porous layer such as fabric so that the medication will be delivered to anal area and then the medication will diffuse out of the porous layer gradually and to be delivered to the rectum after the insertion. A core means will be used to keep the suppository part in shape to be inserted into the rectum and keep it in position until the medication is delivered and the time is to be removed.

C. The suppository to be made from a core as shown at FIG. 21 so that the core will be a delivery means for the medication by having the medication to be stored in a cover, Cover as shown in FIG. 23 and FIG. 24. The cover may be made from materials and media such as fabric, meshes, waxes, hardened medicines or combinations or any other means which can be utilized with these units. This unit will also have the sani pad which will be attached to it as shown in FIG. 23.

D. The suppository to be made from a core as shown at FIG. 15. In this model the outer surface of the core outer has a series of walls, Wall that are arranged in a vertical and horizontal directions which make a series of small spaces, Space that are designed for holding the medication for the delivery to the ano-rectal, or vaginal area. This method prevents medications from moving down and away from the adjacent surface due to gravity, thus it makes the medication more available for the surrounding tissue. This unit also will have the sani pad with or without the med pad as explained in the text.

E. The idea of this invention can be modified by use of this teaching as well as the common art in order to make many other ways of delivery of the medication in the rectal area.

Importantly, the same principles and methods will be also utilized in production of the insert piece of the units for the ladies, so that the insert and its cover will function as the delivery means of the medication for the vulvo-vaginal area.

The use of the sani pads.

This invention also addresses another problems that commonly accompany the hemorrhoids and vulvo-vaginitis and similar surgical problems. In such cases the application of the medication internally and to the outside not only may not reach every inflamed or infected area but also the medication may diffuse and contaminate the opposing dress or underwear. Also, importantly hemorrhoids and vulvo-vaginitis the affected areas are both internal and external thus the use of medication internally may not be effective for the external problems most of the times and it will contamination the underwear. For such reasons this new method combines the use of the suppository with means of application of medicine to the adjacent and the external areas for a more effective treatment. This units consist of the following.

1. A pad means reffered as sanitation pad or sani pad as shown in FIGS. 12 and 13 that consist of a soft, absorbent layer that will stand in area surrounding the suppository means. This layer will be a comfortable means which stay around the anal area.

The pad means has a protective cover outside, made from a thin layer of impermeable material, IL-B such as vinyl, aluminium, latex etc., that prevents from leaking of the oily material and secretions outside and the contamination of the skin. The central part of the sani pad may hold some amount of the medication for delivering to the anal area.

2. A smaller pad means, which is a medicated pad, Med Pad shown in FIGS. 12 and 13 which is located in the center of the Sani Pad. This pad will hold medication for application to the anal or vaginal area. The Med Pad consist a soft layer for holding the medication for the anal area, also it may have a layer of impermeable layer shown at IL-A made from a layer of polymer or thin aluminium or similar.

Importantly, the medicated pad may be omitted in some models. Also in some models the medicated pads may not have the impermeable layer, IL-A The Sani Pad and its related parts will provide the following functions:

I. Providing medication to the skin and mucosa around the orifice.

II. To prevent from the leakage of the medication so that there will be no soling of the underwear or the garment.

III. May provide a gentle massage in the inflamed area to the patient in cases in which he/she feels that this would be helpful.

IV. To cause the medication to come in contact with the folds of the outside area.

The method of preventing these units from falling.

In order to prevent these units from falling from the location of use the following methods and means will be used.

1. The sani pad may have a zone of adhesive as shown at ADH at FIG. 26, that will allow it to be adhered to the skin and prevent it from falling.

2. The sani pad, Sani Pad may have a band similar to the Band shown at FIG. 26 or number of bands that will go around the body in order to keep the sani pad in place.

3. The user will use a tight shorts that will keep the pad inside and prevent it from falling to the pants or from the body down in a wrong circumstance. In some models the sani pad may be attached or adhered to the shorts and prevent it from free fall. Such method is shown at FIG. 27 which shows a zone of attachment means, ATM on it. This is a zone of hook, fastener attachment means that will attach to a matching zone of loop fastener attachment means located inside the underwear of the user. So that this attachment will prevent this unit to fall in a wrong place.

Importantly, various important parts of these inventions are explained in the text which will not be duplicated here to prevent a lengthy application.

Importantly, the packages of the special medication pad and suppositories may have shorts that will be used with these units for the purpose of keeping the used special medication pad and suppository in place after use. So that the user will have every part conveniently in one package.

The related accessories and convenient packages.

This is to make combined units and packages that will be conveniently readily available for a suffering patient to use and to get relief as rapidly as possible. For this purpose, these units will be packed with accompanying required units, pieces and directions as follows:

The Unit for Females

1. A large swab will be provided to be used to remove the pus and secretions that are commonly found in the infected area. This swab, "Swab A", will have a surface covered by an absorbent material such as sterile cotton, gauze or similar material, and will be shaped like a round cylinder of about 15-25 mm diameter and 6-10 cm long. This swab is to be first inserted into the vagina in order to clean/remove the pus, secretions and similar materials from the inflamed area when they are significant.

Importantly, the inner core of these sticks may be made to be an empty balloon or a hollow plastic in order to prevent waste of cotton and absorbent materials which are naturally expensive. Again, the function of this swab is to clean the secretions from the area and to remove thousands and millions of germs by removing copious material. This piece will be removed to be followed by the use of another swab; "Swab B".

2. Swab B will be similar to the one mentioned above; however this swab will have solutions of a mild bactericidal/bacteriostatic or anti-fungal medication, or it will be soaked inside the accompanying bottle of such solutions, which may even be a sterile solution of vinegar, which is commonly used in females. This goal may also be reached by having a clean swab A be soaked in the accompanying small bottle of medication, which is scheduled to be used so that the use of such medicated swabs will prepare the area significantly for the use of the medicated units. This process by itself may cause significant relief in suffering patients. If it does not, then a third swab "Swab C" is scheduled to be used.

3. The Swab C will be similar to the one mentioned above in Swab B; however, this swab will have solutions of a mild local anesthetic, such as Xylocaine, which will be used to give even more relief before insertion of the medicated suppository. This goal may also be reached by having the clean swab A be soaked in the accompanying small bottle of such solution that the patient will receive fast relief from the hurting problem even before the medicated unit is inserted.

4. Educational material, such as written materials, tapes or video cassettes, will be provided to help an unfamiliar woman learn the appropriate use and related information.

5. The needed medicated pad or other units will be included as well.

Units for Draining Pus and Other Secretions

Importantly, this basic unit of medication pad will be altered to make them useful in conditions in which there are secretions such as pus, blood, drainage of different kinds that need to come out, or be drained outside, from a wound. In such circumstances, the area of the wound is commonly covered by a gauze to allow the secretions to be absorbed. In some cases, a piece of gauze would be left in the wound to prevent closure of the opening and for drainage. However, in the applicant's mind, covering such areas with a flat gauze is not the best practice since the gauze itself (especially when it gets somewhat saturated) will be less absorbent and will not allow the drainage to continue in full steam.

The applicant indicates that: "If we want to fully drain pus and other secretions from such wounds, then we should not press the opening of the wound by covering it with flat dressing. Among many things, it may even press the fluid to the surrounding tissues to some degree." In fact, this applicant suggests the use of appropriately shaped balloons or bubbles to press the sides of the ulcerated areas and draining the wounds gently for better drainage. Therefore, based on this basic reasoning the applicant introduces the following models:

1. A model of wound dressing and medicated pads in which the center of the dressing or the medication pad will have a rather empty area to accept and contain the secretions.

2. A model that has an opening in its center. This opening is connected to a suction cup. When activated, squeezed and released, this suction cup will suck the secretions inside itself. The inner space of this suction cup may have an absorbing mesh to absorb and hold the suctioned materials inside. The appropriately-shaped pressurized balloon, or a series of balloons or pressured soft bubbles, are used around the secretion area in order to increase the pressure to a reasonable and appropriate level to facilitate drainage of the secretions in the center. These units may be made in the shape of doughnuts or long pieces (like a soft doughnut-shaped balloon which is pulled from two opposing points to be long and still have an empty center) with an empty center to allow pressure to be applied in the sides of the wound. These medicated pads may have a cut in the side to allow the unit to be inserted easily if a draining unit has to go into its center.

Importantly, these units may have bands, straps or wraps in their sides to allow them to be wrapped and be held in the needed site securely and appropriately. A sleeve made from latex may be used to perform this function as well.

Importantly, the suctioning function of this unit may be done by a small pump that creates a steady lower level negative pressure that can be connected to the center of the unit by a tube. Also, other methods to create a vacuum such as vacuum bottles may be used in certain conditions to do this job properly if it is applicable. One particular model of this unit may be made with a two-layered pad connected to a special balloon that will be entered inside the rectum to pass the anal sphincter and then to get larger and flat after being blown in order to prevent the stool from leaking around the anal sphincter in incontinent cases. The balloon will be inflated after insertion into the rectum.

Use of Degradable or Retractable Cores

The applicant also introduces suppositories that their cores will not occupy the rectum after use or it will be negligible. These models can be as follows.

1. The core may be made from a degradable material made from medication or inert material that will be absorbed or disintegrated after the use, due to effect of the heat, moisture, enzymes or any other possible means.

2. The core may have a very low profile body such as a piece of thread or similar so that after the delivery of the medication the remaining will not be significant to cause problem it the area.

3. A retractable means such as a elastic piece that will be in a pulled condition inside the medicine and will retract after the medication is used up and the elastic piece is free.

Importantly, the type of medication is not limited to one form or effect or another and can be chosen to be of any form or effect.

Please note in order to prevent from a lengthy text, not all the information which was in the figures are repeated in the explanation of the invention. However, the main body of the idea can be noted from the information in the figures. The applicant is going to modify this application for presenting it as a regular application and he will modify the text at that time. Please note that importantly, the methods and teachings in this application would make it possible to make many models of similar units in order to do the functions that are explained here. The claims will be provided with regular application.

Importantly, the size, pattern, shape thickness, materials and every other important characteristics of the models explained in this text may vary in order for making the best possible working models.

The invention claimed is:

1. A device for delivering medication both to an internal body cavity and to external tissue surrounding a body orifice that opens to the cavity, the device comprising:
   an elongated body that has a proximal end and a distal end and that can be inserted through the orifice to place the elongated body within the cavity for delivering medication to a wall of the cavity,
   a pad that circumferentially surrounds the proximal end of the elongated body and that comprises a distal face which, when the elongated body is placed within the cavity, is placed against tissue surrounding the orifice for delivering medication to that tissue, the pad comprising a proximal face opposite the distal face,
   a first impermeable layer which comprises a distal face disposed against the proximal face of the pad, the first impermeable layer further comprising a proximal face opposite its distal face,
   a further layer having a distal face disposed against the proximal face of the impermeable layer and presenting absorbent material to the tissue surrounding the orifice bond an outer perimeter of the pad, the further layer having a proximal face opposite its distal face,
   a second impermeable layer having a distal face covering the proximal face of the further layer, and
   in which the elongated body comprises a central core that forms the bulk of the elongated body to maintain the shape of the elongated body during passage through the orifice as it is entering the cavity and a cover covering the central core.

2. A device as set forth in claim 1 in which the central core comprises a neck that passes through the pad, the first impermeable layer, the further layer, and the second impermeable layer, and the device further comprising a base that joins with the neck and is disposed against a proximal face of the second impermeable layer that is opposite its distal face.

3. A device as set forth in claim 2 in which the neck is constructed to allow a portion of the central core covered by the cover to flex relative to the base.

4. A device as set forth in claim 2 in which the base is longer in one direction than in another direction that is at 90 degrees to the one direction.

5. A device for delivering medication both to an internal body cavity and to external tissue surrounding a body orifice that opens to the cavity, the device comprising:
   an elongated body that has a proximal end and a distal end and that can be inserted through the orifice to place the elongated body within the cavity for delivering medication to a wall of the cavity,
   a pad that circumferentially surrounds the proximal end of the elongated body and that comprises a distal face which, when the elongated body is placed within the cavity, is placed against tissue surrounding the orifice for delivering medication to that tissue, the pad comprising a proximal face opposite the distal face,
   a first impermeable layer which comprises a distal face disposed against the proximal face of the pad, the first impermeable layer further comprising a proximal face opposite its distal face,
   a further layer having a distal face disposed against the proximal face of the impermeable layer and presenting absorbent material to the tissue surrounding the orifice beyond an outer perimeter of the pad, the further layer having a proximal face opposite its distal face,
   a second impermeable layer having a distal face covering the proximal face of the further layer, and further comprising a cover that comprises a series of walls that form a series of spaces on the outside of the cover within which medication can be disposed.

* * * * *